US010058143B2

(12) United States Patent
Walborn et al.

(10) Patent No.: US 10,058,143 B2
(45) Date of Patent: Aug. 28, 2018

(54) OUTSOLE FOR ORTHOPEDIC DEVICE (71) Applicant: OSSUR HF, Reykjavik (IS)

(72) Inventors: Jonathan Walborn, Mission Viejo, CA (US); Harry Duane Romo, Aliso Viejo, CA (US); Adam Dunn, Laguna Niguel, CA (US)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 14/566,842

(22) Filed: Dec. 11, 2014

(65) Prior Publication Data

US 2015/0164179 A1    Jun. 18, 2015

Related U.S. Application Data (60) Provisional application No. 61/915,011, filed on Dec. 12, 2013.

(51) Int. Cl.
    *A61F 5/00*     (2006.01)
    *A43B 13/14*    (2006.01)
    *A61F 5/01*     (2006.01)

(52) U.S. Cl.
    CPC ............ *A43B 13/14* (2013.01); *A43B 13/145* (2013.01); *A61F 5/0111* (2013.01); *A61F 5/0195* (2013.01)

(58) Field of Classification Search
    CPC ..... A43B 13/14; A43B 13/145; A61F 5/0195; A61F 5/0111

(Continued)

(56) References Cited

U.S. PATENT DOCUMENTS 975,576 A    11/1910  Sexton
1,012,017 A  12/1911  Salt
(Continued)

FOREIGN PATENT DOCUMENTS

CN    101711141 A    5/2010
CN    102026592 A    4/2011
(Continued)

OTHER PUBLICATIONS

International Search Report and Written Opinion from International Application No. PCT/US2014/069686, dated Mar. 13, 2015.
(Continued)

*Primary Examiner* — Katharine Gracz
(74) *Attorney, Agent, or Firm* — Workman Nydegger (57) ABSTRACT An outsole for an orthopedic device includes a heel part, a forefoot part, and a mid-foot part separating the heel part from the forefoot part. A longitudinal axis extends in a longitudinal direction between an anterior end of the forefoot part and a posterior end of the heel part. A transverse axis intersects the longitudinal axis and extends in a transverse direction between a lateral edge of the outsole and a medial edge of the outsole. A bottom surface extends along the longitudinal axis and between the medial and lateral edges. The bottom surface defines an apex at the intersection of the longitudinal and transverse axes and at least one apical line passing through the apex and subtending an oblique angle to the longitudinal axis. The bottom surface curves through the apex and along the at least one apical line in both the longitudinal and transverse directions.

17 Claims, 7 Drawing Sheets (58) Field of Classification Search
USPC .................. 482/79; 602/23, 28, 29; D2/951
See application file for complete search history.

(56) References Cited

U.S. PATENT DOCUMENTS

| | | | |
|---|---|---|---|
| 2,200,849 A | 5/1940 | Margolin |
| 2,236,367 A | 3/1941 | Gruber |
| 2,292,297 A | 8/1942 | Sherlock |
| 2,444,640 A | 7/1948 | Epstein |
| 2,868,191 A | 1/1959 | Juhasz |
| 2,885,797 A | 5/1959 | Chrencik |
| 2,888,016 A | 5/1959 | De Lamater |
| 2,909,854 A | 10/1959 | Edelstein |
| 2,913,837 A | 11/1959 | Geuder |
| 2,917,844 A | 12/1959 | Scholl |
| 2,928,193 A | 3/1960 | Kristan |
| 2,979,835 A | 4/1961 | Scholl |
| 2,979,836 A | 4/1961 | Scholl |
| 3,270,358 A | 9/1966 | Milner |
| 3,464,126 A | 9/1969 | Sarkissian |
| 3,548,420 A | 12/1970 | Spence |
| 3,580,248 A | 5/1971 | Larson |
| 3,681,860 A | 8/1972 | Bidegain |
| 3,685,176 A | 8/1972 | Rudy |
| 3,730,169 A | 5/1973 | Fiber |
| 3,735,758 A | 5/1973 | Novotney |
| 3,760,056 A | 9/1973 | Rudy |
| 3,786,805 A | 1/1974 | Tourin |
| 3,792,537 A | 2/1974 | Plank et al. |
| 3,814,088 A | 6/1974 | Raymond |
| 3,834,377 A | 9/1974 | Lebold |
| 3,859,740 A | 1/1975 | Kemp |
| 3,922,800 A | 12/1975 | Miller et al. |
| 3,955,565 A | 5/1976 | Johnson, Jr. |
| 4,045,888 A | 9/1977 | Oxenberg |
| 4,057,056 A | 11/1977 | Payton |
| 4,095,353 A | 6/1978 | Foldes |
| 4,100,686 A | 7/1978 | Sgarlato et al. |
| 4,142,307 A | 3/1979 | Martin |
| 4,177,583 A | 12/1979 | Chapman |
| 4,184,273 A | 1/1980 | Boyer et al. |
| 4,217,706 A | 8/1980 | Vartanian |
| 4,217,893 A | 8/1980 | Payton |
| 4,232,459 A | 11/1980 | Vaccari |
| 4,237,626 A | 12/1980 | Brown |
| 4,267,649 A | 5/1981 | Smith |
| 4,300,294 A | 11/1981 | Riecken |
| 4,333,248 A | 6/1982 | Samuels |
| 4,370,818 A | 2/1983 | Simoglou |
| 4,408,402 A | 10/1983 | Looney |
| 4,414,965 A | 11/1983 | Mauldin et al. |
| D272,281 S | 1/1984 | Alush |
| 4,446,856 A | 5/1984 | Jordan |
| 4,494,536 A | 1/1985 | Latenser |
| 4,505,269 A | 3/1985 | Davies et al. |
| 4,550,721 A | 11/1985 | Michel |
| 4,565,017 A | 1/1986 | Ottieri |
| 4,571,853 A | 2/1986 | Medrano |
| 4,572,169 A | 2/1986 | Mauldin et al. |
| 4,587,962 A | 5/1986 | Greene et al. |
| 4,598,484 A | 7/1986 | Ma |
| 4,599,811 A | 7/1986 | Rousseau |
| 4,608,768 A | 9/1986 | Cavanagh |
| 4,620,378 A | 11/1986 | Sartor |
| 4,633,598 A | 1/1987 | Moronaga et al. |
| 4,633,599 A | 1/1987 | Morell et al. |
| 4,633,877 A | 1/1987 | Pendergast |
| 4,660,300 A | 4/1987 | Morell et al. |
| 4,669,202 A | 6/1987 | Ottieri |
| 4,674,204 A | 6/1987 | Sullivan et al. |
| 4,674,205 A | 6/1987 | Anger |
| 4,677,767 A | 7/1987 | Darby |
| 4,680,878 A | 7/1987 | Pozzobon et al. |
| 4,689,898 A | 9/1987 | Fahey |
| 4,719,710 A | 1/1988 | Pozzobon |
| 4,727,661 A | 3/1988 | Kuhn |
| 4,741,115 A | 5/1988 | Pozzobon |
| 4,748,726 A | 6/1988 | Schoch |
| 4,760,653 A | 8/1988 | Baggio |
| 4,771,768 A | 9/1988 | Crispin |
| 4,773,170 A | 9/1988 | Moore et al. |
| 4,793,078 A | 12/1988 | Andrews |
| D299,787 S | 2/1989 | Bates |
| 4,805,321 A | 2/1989 | Tonkel |
| 4,805,601 A | 2/1989 | Eischen, Sr. |
| 4,811,504 A * | 3/1989 | Bunke .................. A43B 5/0419 36/132 |
| 4,869,001 A | 9/1989 | Brown |
| 4,872,273 A | 10/1989 | Smeed |
| 4,879,822 A | 11/1989 | Hayes |
| 4,893,418 A | 1/1990 | Ogden |
| 4,934,355 A | 6/1990 | Porcelli |
| 4,947,838 A | 8/1990 | Giannetti |
| 4,974,583 A | 12/1990 | Freitas |
| 5,065,481 A | 11/1991 | Walkhoff |
| 5,065,531 A | 11/1991 | Prestridge |
| 5,078,128 A | 1/1992 | Grim et al. |
| 5,123,180 A | 6/1992 | Nannig et al. |
| 5,125,400 A | 6/1992 | Johnson, Jr. |
| D329,527 S | 9/1992 | Cohen |
| 5,143,058 A | 9/1992 | Luber et al. |
| D330,109 S | 10/1992 | Hatfield |
| 5,152,038 A | 10/1992 | Schoch |
| 5,154,682 A | 10/1992 | Kellerman |
| 5,154,695 A | 10/1992 | Farris et al. |
| 5,157,813 A | 10/1992 | Carroll |
| 5,176,623 A | 1/1993 | Stetman et al. |
| 5,176,624 A | 1/1993 | Kuehnreich |
| 5,183,036 A | 2/1993 | Spademan |
| 5,197,942 A | 3/1993 | Brady |
| D334,646 S | 4/1993 | Dissinger |
| D337,876 S | 8/1993 | Kilbey |
| 5,233,767 A | 8/1993 | Kramer |
| 5,242,379 A | 9/1993 | Harris et al. |
| 5,257,470 A | 11/1993 | Auger et al. |
| 5,277,695 A | 1/1994 | Johnson, Jr. et al. |
| D344,589 S | 2/1994 | Kilbey |
| 5,288,286 A | 2/1994 | Davis et al. |
| 5,325,613 A | 7/1994 | Sussmann |
| 5,329,705 A | 7/1994 | Grim et al. |
| D352,191 S | 11/1994 | Zorian |
| D352,784 S | 11/1994 | Cohen et al. |
| 5,359,791 A | 11/1994 | Prahl et al. |
| 5,368,549 A | 11/1994 | McVicker |
| 5,368,551 A | 11/1994 | Zuckerman |
| 5,370,133 A | 12/1994 | Darby et al. |
| 5,378,223 A | 1/1995 | Grim et al. |
| 5,399,152 A | 3/1995 | Habermeyer et al. |
| 5,407,421 A | 4/1995 | Goldsmith |
| 5,425,701 A | 6/1995 | Oster et al. |
| 5,426,872 A | 6/1995 | Hayes |
| 5,429,377 A | 7/1995 | Duer |
| 5,429,588 A | 7/1995 | Young et al. |
| 5,433,695 A * | 7/1995 | Drennan ............... A61F 13/045 36/15 |
| 5,435,009 A | 7/1995 | Schild et al. |
| 5,438,768 A | 8/1995 | Bauerfeind |
| 5,441,015 A | 8/1995 | Farley |
| D363,780 S | 10/1995 | Darby et al. |
| 5,464,385 A | 11/1995 | Grim |
| 5,477,593 A | 12/1995 | Leick |
| D365,919 S | 1/1996 | Chen |
| 5,483,757 A | 1/1996 | Frykberg |
| 5,496,263 A | 3/1996 | Fuller, II et al. |
| 5,548,848 A | 8/1996 | Huybrechts |
| D373,548 S | 9/1996 | Losi, II |
| 5,558,627 A | 9/1996 | Singer et al. |
| D375,191 S | 11/1996 | Tonkel et al. |
| 5,577,998 A | 11/1996 | Johnson, Jr. et al. |
| D376,429 S | 12/1996 | Antar |
| 5,617,650 A | 4/1997 | Grim |
| D379,258 S | 5/1997 | Cheng |
| 5,641,322 A | 6/1997 | Silver et al. |
| 5,647,104 A | 7/1997 | James |

(56) References Cited

U.S. PATENT DOCUMENTS

| | | |
|---|---|---|
| 5,656,226 A | 8/1997 | McVicker |
| D383,250 S | 9/1997 | Amico |
| D384,746 S | 10/1997 | Varn |
| D390,345 S | 2/1998 | Aird et al. |
| 5,717,996 A | 2/1998 | Feldmann |
| D391,748 S | 3/1998 | Koh |
| 5,761,834 A | 6/1998 | Grim et al. |
| 5,778,563 A | 7/1998 | Ahlbaumer |
| 5,778,565 A | 7/1998 | Holt et al. |
| 5,797,862 A | 8/1998 | Lamont |
| D398,142 S | 9/1998 | Benoit |
| D398,439 S | 9/1998 | McDonald |
| 5,819,378 A | 10/1998 | Doyle |
| 5,827,210 A | 10/1998 | Antar et al. |
| 5,827,211 A | 10/1998 | Sellinger |
| D401,042 S | 11/1998 | Davis |
| 5,833,639 A | 11/1998 | Nunes et al. |
| 5,836,902 A | 11/1998 | Gray |
| 5,846,063 A | 12/1998 | Lakic |
| 5,853,380 A | 12/1998 | Miller |
| 5,857,987 A | 1/1999 | Habermeyer |
| D404,895 S | 2/1999 | Rosato |
| 5,868,690 A | 2/1999 | Eischen, Sr. |
| 5,913,841 A | 6/1999 | Lamont |
| 5,934,599 A | 8/1999 | Hammerslag |
| 5,951,504 A | 9/1999 | Iglesias et al. |
| 5,961,477 A | 10/1999 | Turtzo |
| 5,993,404 A | 11/1999 | McNiel |
| 6,000,148 A | 12/1999 | Cretinon |
| D418,967 S | 1/2000 | Stengel |
| 6,021,780 A | 2/2000 | Darby |
| 6,027,468 A | 2/2000 | Pick |
| 6,044,578 A | 4/2000 | Kelz |
| 6,098,315 A | 8/2000 | Hoffmann, III |
| 6,202,953 B1 | 3/2001 | Hammerslag |
| 6,205,685 B1 | 3/2001 | Kellerman |
| 6,228,044 B1 | 5/2001 | Jensen et al. |
| 6,267,742 B1 | 7/2001 | Krivosha et al. |
| RE37,338 E | 8/2001 | McVicker |
| 6,289,558 B1 | 9/2001 | Hammerslag |
| 6,334,854 B1 | 1/2002 | Davis |
| 6,338,768 B1 | 1/2002 | Chi |
| 6,361,514 B1 | 3/2002 | Brown et al. |
| 6,377,178 B1 | 4/2002 | Detoro et al. |
| 6,409,691 B1 | 6/2002 | Dakin et al. |
| 6,432,073 B2 | 8/2002 | Pior et al. |
| D467,708 S | 12/2002 | Portzline |
| D473,654 S | 4/2003 | Iglesias et al. |
| D473,704 S | 4/2003 | Wilson |
| 6,572,571 B2 | 6/2003 | Lowe |
| D476,799 S | 7/2003 | Fuerst |
| 6,589,194 B1 | 7/2003 | Calderon et al. |
| 6,682,497 B2 | 1/2004 | Jensen et al. |
| 6,755,798 B2 | 6/2004 | McCarthy et al. |
| 6,792,699 B2 | 9/2004 | Long et al. |
| D500,855 S | 1/2005 | Pick et al. |
| 6,866,043 B1 | 3/2005 | Davis |
| D504,005 S * | 4/2005 | Schoenborn ............ D2/952 |
| D505,727 S | 5/2005 | Krahner et al. |
| 6,945,944 B2 | 9/2005 | Kuiper et al. |
| 6,976,972 B2 | 12/2005 | Bradshaw |
| 6,991,613 B2 | 1/2006 | Sensabaugh |
| 7,010,823 B2 | 3/2006 | Baek |
| 7,018,351 B1 | 3/2006 | Iglesias et al. |
| D528,214 S | 9/2006 | Binet |
| 7,198,610 B2 | 4/2007 | Ingimundarson et al. |
| 7,281,341 B2 | 10/2007 | Reagan et al. |
| 7,288,076 B2 | 10/2007 | Grim et al. |
| D554,835 S | 11/2007 | Peydro |
| D555,343 S | 11/2007 | Bettencourt |
| 7,303,538 B2 | 12/2007 | Grim et al. |
| 7,311,686 B1 | 12/2007 | Iglesias et al. |
| 7,354,411 B2 | 4/2008 | Perry et al. |
| RE40,363 E | 6/2008 | Grim et al. |
| 7,384,584 B2 | 6/2008 | Jerome et al. |
| D575,039 S | 8/2008 | Amado et al. |
| 7,418,755 B2 | 9/2008 | Bledsoe et al. |
| D583,956 S | 12/2008 | Chang et al. |
| 7,493,706 B2 | 2/2009 | Cho et al. |
| D592,755 S | 5/2009 | Chang et al. |
| D592,756 S | 5/2009 | Chang et al. |
| D594,638 S * | 6/2009 | Butler ............ D2/952 |
| D596,301 S | 7/2009 | Campos et al. |
| D596,386 S | 7/2009 | Brambilla |
| 7,591,050 B2 | 9/2009 | Hammerslag |
| D603,155 S | 11/2009 | Della Valle et al. |
| D614,775 S | 4/2010 | Snively |
| D615,285 S | 5/2010 | Martin |
| D616,556 S | 5/2010 | Hu |
| 7,717,869 B2 | 5/2010 | Eischen, Sr. |
| 7,727,174 B2 | 6/2010 | Chang et al. |
| D622,494 S | 8/2010 | Warren |
| 7,838,717 B2 | 11/2010 | Haggstrom et al. |
| D634,438 S | 3/2011 | Hu |
| D634,852 S | 3/2011 | Hu |
| D636,157 S | 4/2011 | Nascimento |
| D636,159 S | 4/2011 | Petrie |
| 7,964,766 B2 | 6/2011 | Blott et al. |
| D642,363 S | 8/2011 | Rajmohan et al. |
| D642,775 S | 8/2011 | Raysse |
| 8,002,724 B2 | 8/2011 | Hu et al. |
| 8,012,112 B2 | 9/2011 | Barberio |
| 8,021,347 B2 | 9/2011 | Vitaris et al. |
| D648,113 S | 11/2011 | Chang |
| D651,381 S | 1/2012 | Simms |
| 8,158,844 B2 | 4/2012 | McNeil |
| D661,887 S | 6/2012 | Petrie |
| 8,308,705 B2 | 11/2012 | Lin et al. |
| 8,313,449 B2 | 11/2012 | Hardman et al. |
| D675,421 S | 2/2013 | Petrie |
| D677,866 S | 3/2013 | Vestuti et al. |
| D680,728 S | 4/2013 | Stryjak |
| D682,517 S | 5/2013 | Taylor |
| D683,214 S | 5/2013 | McAdam |
| 8,506,510 B2 | 8/2013 | Hu et al. |
| D689,677 S * | 9/2013 | Bathum ............ D2/951 |
| 8,574,181 B2 | 11/2013 | Bird et al. |
| D696,499 S | 12/2013 | Lehtinen |
| D696,785 S | 12/2013 | Weaver, II et al. |
| D698,074 S | 1/2014 | Hargreaves |
| D698,338 S | 1/2014 | Ingham et al. |
| D701,032 S | 3/2014 | Leleu |
| D701,033 S | 3/2014 | Leleu |
| D703,335 S | 4/2014 | Bird et al. |
| D712,639 S | 9/2014 | Spring |
| D714,042 S | 9/2014 | Petrie |
| 9,003,677 B2 * | 4/2015 | Goodsmith ............ A43B 3/108 |
| | | 36/103 |
| 9,220,621 B2 | 12/2015 | Hu et al. |
| 9,220,622 B2 | 12/2015 | Ingimundarson et al. |
| 9,333,106 B2 | 5/2016 | Hu et al. |
| 9,468,553 B2 | 10/2016 | Hu et al. |
| 9,492,301 B2 | 11/2016 | Hu et al. |
| 2002/0095105 A1 | 7/2002 | Jensen |
| 2002/0095750 A1 | 7/2002 | Hammerslag |
| 2002/0128574 A1 | 9/2002 | Darby |
| 2003/0093882 A1 | 5/2003 | Gorza et al. |
| 2003/0171703 A1 | 9/2003 | Grim et al. |
| 2003/0204938 A1 | 11/2003 | Hammerslag |
| 2004/0010212 A1 | 1/2004 | Kuiper et al. |
| 2004/0019307 A1 | 1/2004 | Grim et al. |
| 2004/0167453 A1 | 8/2004 | Peters |
| 2005/0131324 A1 | 6/2005 | Bledsoe |
| 2005/0145256 A1 | 7/2005 | Howard et al. |
| 2005/0165338 A1 | 7/2005 | Iglesias et al. |
| 2005/0171461 A1 | 8/2005 | Pick |
| 2005/0172517 A1 | 8/2005 | Bledsoe et al. |
| 2005/0274046 A1 | 12/2005 | Schwartz |
| 2006/0084899 A1 | 4/2006 | Verkade et al. |
| 2006/0135899 A1 | 6/2006 | Jerome et al. |
| 2006/0135902 A1 | 6/2006 | Ingimundarson et al. |
| 2006/0156517 A1 | 7/2006 | Hammerslag et al. |
| 2006/0189907 A1 | 8/2006 | Pick et al. |
| 2006/0217649 A1 | 9/2006 | Rabe |

(56) References Cited

U.S. PATENT DOCUMENTS

| | | |
|---|---|---|
| 2006/0229541 A1 | 10/2006 | Hassler et al. |
| 2007/0167884 A1 | 7/2007 | Viangrum et al. |
| 2007/0169378 A1 | 7/2007 | Sodeberg et al. |
| 2007/0185425 A1 | 8/2007 | Einarsson et al. |
| 2007/0191749 A1 | 8/2007 | Barberio |
| 2007/0282230 A1 | 12/2007 | Valderrabano et al. |
| 2007/0293798 A1 | 12/2007 | Hu et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0294082 A1 | 11/2008 | Chang et al. |
| 2008/0294083 A1 | 11/2008 | Chang et al. |
| 2009/0012482 A1 | 1/2009 | Pinto et al. |
| 2009/0270820 A1 | 10/2009 | Johnson et al. |
| 2009/0287127 A1 | 11/2009 | Hu et al. |
| 2009/0287128 A1 | 11/2009 | Ingimundarson et al. |
| 2010/0069808 A1 | 3/2010 | Mitchell |
| 2010/0100020 A1* | 4/2010 | Fout ................ A61F 5/0111 602/23 |
| 2010/0234782 A1 | 9/2010 | Hu et al. |
| 2010/0324461 A1 | 12/2010 | Darby, II et al. |
| 2011/0009791 A1 | 1/2011 | Hopmann |
| 2011/0015555 A1 | 1/2011 | Anderson et al. |
| 2011/0196275 A1 | 8/2011 | Chang et al. |
| 2012/0010534 A1 | 1/2012 | Kubiak et al. |
| 2012/0035560 A1 | 2/2012 | Eddy et al. |
| 2012/0078148 A1 | 3/2012 | Hu et al. |
| 2012/0220960 A1 | 8/2012 | Ruland |
| 2012/0238924 A1 | 11/2012 | Avni |
| 2013/0066247 A1 | 3/2013 | Bird et al. |
| 2013/0310721 A1 | 11/2013 | Hu et al. |
| 2014/0171837 A1 | 6/2014 | Harcourt |
| 2014/0276310 A1 | 9/2014 | Grim et al. |

FOREIGN PATENT DOCUMENTS

| | | |
|---|---|---|
| DE | 23 41 658 A1 | 3/1974 |
| DE | 32 287 53 A1 | 2/1984 |
| EP | 0 095 396 A1 | 11/1983 |
| EP | 0 201 051 A1 | 11/1986 |
| EP | 0770368 A1 | 5/1997 |
| EP | 2468323 A1 | 6/2012 |
| FR | 2 399 811 A1 | 3/1979 |
| FR | 2634988 A1 | 2/1990 |
| FR | 2 681 516 A1 | 3/1993 |
| GB | 2 124 473 A | 2/1984 |
| GB | 2 178 940 A | 2/1987 |
| JP | 2005211626 A | 8/2005 |
| WO | 93/13685 A1 | 7/1993 |
| WO | 93/24081 A1 | 12/1993 |
| WO | 94/18863 A1 | 9/1994 |
| WO | 97/36507 A1 | 10/1997 |
| WO | 2004/021817 A1 | 3/2004 |
| WO | 2006035469 A2 | 4/2006 |
| WO | 2006045079 A1 | 4/2006 |
| WO | 2007078845 A2 | 7/2007 |
| WO | 2010104824 A1 | 9/2010 |
| WO | 2013/084213 A1 | 6/2013 |
| WO | 2015006766 A1 | 1/2015 |

OTHER PUBLICATIONS

International Search Report and Written Opinion from International Application No. PCT/US2014/057421, dated Dec. 8, 2014.
International Search Report from PCT Application No. PCT/US2009/003018, dated Jul. 24, 2009.
Product Information Sheet: Nextep Contour Walker, Procare, DJ Orthopedics, Jan. 1, 2008,1 page. Retrieved from the internet, www.djortho.com.
Product Information Sheet: Nextep Contour w/Air Walker, Procare, DJ Orthopedics, Jan. 1, 2008, 1 page. Retrieved from internet, www.djortho.com.
Product Information Sheet: XP Achilles Walker (EU only), Aircast, Jan. 1, 2008, 4 pages. Retrieved from the internet, http://www.aircast.com/index.asp/fuseaction/products.detail/cat/2/id/104.
Product Information Sheet: XP Diabetic Walker System, Aircast, Jan. 1, 2008, 4 pages. Retrieved from the internet, http://www.aircast.com/index.asp/fuseaction/products.detail/cat/2/id/15.
Product Information Sheet: SP Walker (short pneumatic), Aircast, Jan. 1, 2008, 4 pages. Retrieved from the internet, http://www.aircast.com/index.asp/fuseaction/products.detail/cat/2/id/14.
Product Information Sheet: FP Walker (foam pneumatic), Aircast, Jan. 1, 2008, 4 pages. Retrieved from the internet, http://www.aircast.com/index.asp/fuseaction/products.detail/cat/2/id/75.
Product Information Sheet: XP Walker (extra pneumatic), Aircast, Jan. 1, 2008, 4 pages. Retrieved from the internet, http://www.aircast.com/index.asp/fuseaction/products.detail/cat/2/id/76.
International Search Report and Written Opinion for International Application No. PCT/US2014/056201, dated Dec. 5, 2014.
International Search Report from PCT Application No. PCT/US2016/014816, dated Apr. 28, 2016.
European Search Report from corresponding European Application No. EP 15 20 0198.8, dated May 20, 2016.
Chinese Office Action from CN Application No. 201480052921.0, dated Feb. 4, 2017.

* cited by examiner

OUTSOLE FOR ORTHOPEDIC DEVICE

TECHNICAL FIELD

The disclosure relates to an outsole for an orthopedic device.

BACKGROUND

The normal operation of the foot provides a smooth rolling motion through a step when ambulating. In a normal gait, the load on a person's foot moves from heel to toe at an angle from the lateral side or outside of the foot (supination) to the medial side or inside of the foot (pronation). A normal step begins with the heel strike as the heel is set down on the support surface or ground and ends with the toe off as the large toe pushes the foot off the support surface.

Many efforts have been made over the years to construct an outsole for orthopedic devices that promotes a healthy and natural gait. One such outsole construction is tapered or curved directly from back to front in a linear fashion. Such a design initiates a roll-over that is limited to straight ahead from back to front allowing heel strike, rocking straight forward, then toe off. However, most people do not walk with their feet pointed straight ahead. Rather, most people walk with their feet externally rotated. When feet point outward, it is commonly called toed-out or exorotated. When feet point inward, it is commonly called toed-in, a tendency referred to as walking "pigeon toed." Thus, because people do not walk with their feet straight forward, the linear roll-over motion of known outsoles resists the natural gait of the wearer's foot, adding stress and discomfort to the wearer as the wearer ambulates, which may adversely affect recuperation and/or cause undesirable biomechanical compensations which can cause problems for the wearer in the long term. Such problems can include, but are not limited to, bad posture, back problems, an unhealthy gait, foot abnormalities, muscle imbalances in the foot and/or leg, and/or pressure ulcers.

The linear roll-over motion of known outsoles also causes foot and leg fatigue because the action of the outsole conflicts with the natural roll-over motion of the user, requiring the user to adjust or correct the position of the user's foot while walking. It also can create awkward pressure points on the user's lower leg and/or foot as a result of the orthopedic device being urged unnaturally against the user's lower leg and/or foot while walking.

There exists a need for improved outsoles for orthopedic devices that facilitate a more natural and comfortable roll-over motion of a user's foot from heel strike through toe-off.

SUMMARY

The disclosure describes various embodiments of an outsole for an orthopedic device providing a construction and design that facilitates a more natural roll-over motion of the user's foot from heel strike through toe-off. The embodiments described can include an outsole having a heel part, a forefoot part, and a mid-foot part separating the heel part from the forefoot part. A longitudinal axis extends in a longitudinal direction between an anterior end of the forefoot part and a posterior end of the heel part. A transverse axis intersects the longitudinal axis and extends in a transverse direction between a lateral edge of the outsole and a medial edge of the outsole. A bottom surface extends along the longitudinal axis and between the medial and lateral edges.

The bottom surface defines an apex at the intersection of the longitudinal and transverse axes and at least one apical line passing through the apex and subtending an oblique angle to the longitudinal axis. The bottom surface curves along the at least one apical line in both the longitudinal and transverse directions.

The curvature of the bottom surface in both the longitudinal and transverse directions creates a roll-over surface that offers reduced or little resistance to the natural roll-over motion of the user's foot rather than forcing the foot to roll-over straight ahead from back to front as in the prior art, which can create strain on the knee and/or other joints. It also provides a smoother and more comfortable ride for the user by accommodating exorotated lines of progression or other lines of progression rotated relative to the longitudinal axis and accounting for common gait dynamics which known outsoles fail to do.

According to a variation, the radius of curvature of the bottom surface along different apical lines is substantially the same. Because of this, the user's foot can experience the same or a similar roll-over motion on the outsole along different lines of progression corresponding to the apical lines. This encourages a more natural and smoother roll-over of the user's foot because the foot can just as easily and comfortably roll-over along one line of progression as another.

According to a variation, a tread section is on the bottom surface that defines an interior region arranged for accommodating at least a portion of different lines of progression corresponding to the apical lines. This helps reduce wearing of the bottom surface preferentially along the different lines of progression by transferring and/or distributing at some of the contact forces along the lines of progression to the surrounding tread section.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

These and other features, aspects, and advantages of the present disclosure will become better understood regarding the following description, appended claims, and accompanying drawings.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the embodiments disclosed, but on the contrary, that the intention covers all modifications, alternative constructions, combinations, and equivalents falling within the spirit and scope of the disclosure.

For further ease of understanding the embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and that in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however, such support members or shells may have some degree of flexibility or resiliency.

The exemplary embodiments of an outsole can be used in various orthopedic devices, including, but not limited to, configurations of walkers or walking boots, post-surgical shoes, diabetic shoes, or any other suitable orthopedic device.

Figure 1:
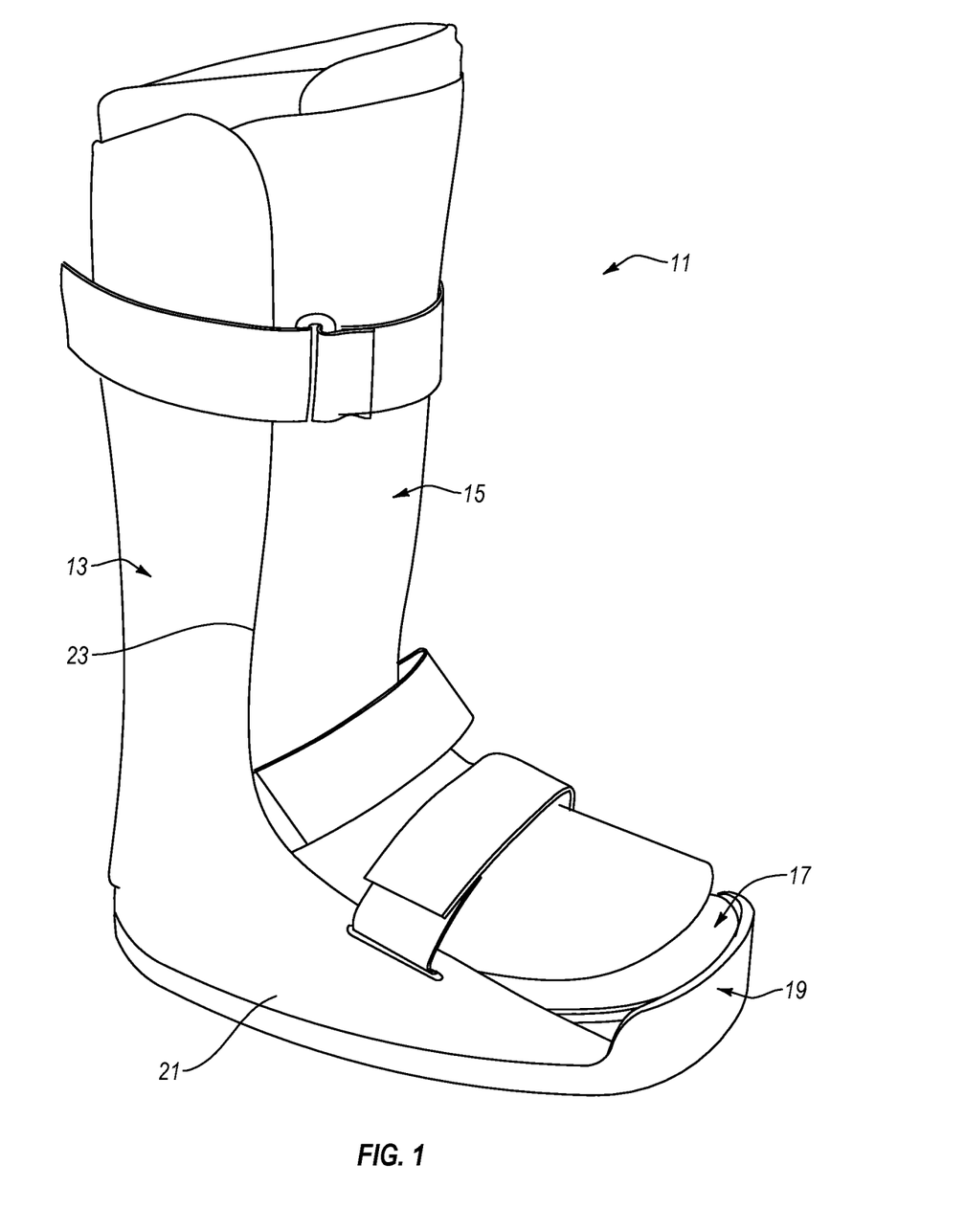
FIG. 1 is a front isometric view of a walker with the straps removed according to an embodiment.

For instance, exemplary embodiments of an outsole can be implemented with an orthopedic device comprising a walker 11, as shown in FIG. 1. An exemplary walker can include a base shell 13 including a plantar portion 21 and defining an opening 23 over a dorsal aspect thereof. A dorsal shell 15 can be contoured to generally correspond to the opening 23 of the base shell 13, such that the lower leg is generally fully enclosed and supported by the walker 11. The dorsal shell 15 can be moveable away and towards the base shell 13 in order to open and close the walker 11. An insole 17 can be situated in a foot bed of the walker 11. In this exemplary device 11, an outsole 19 can be provided along the distal plantar surface 21 of the base shell 13. While a circumferential walker is shown, it will be appreciated that other walkers (e.g., a strut walker) may utilize similar outsole configurations.

Referring now to FIGS. 2-9, an exemplary embodiment of an outsole 100 includes and a sole portion 110 including a bottom surface 116 and an upper surface 118 opposite the bottom surface 116. The sole portion 110 may define a height or thickness between the upper surface 118 and the bottom surface 116. The upper surface 118 may be shaped and configured to be secured to and to span a length of the plantar portion 21 of the base shell 13.

The outsole 100 can be attached to the base shell 13 in any suitable manner. The upper surface 118 can be bonded to the plantar portion 21 of the base shell 13 by adhesive, and one or more edges of the upper surface 118 can extend around and up the sides of the plantar portion 21. The outsole 100 can be integrally formed or attached along the plantar portion 21 of the base shell 13, for example, via overmolding or any other suitable two-shot molding process.

A toe protector portion 120 can be located at a toe end portion of the plantar portion of the base shell 13 and can extend generally upright and perpendicular relative to the sole portion 110 and above the toe end portion of the base shell 13. A heel section 125 is arranged to extend over at least a heel or posterior end of the plantar portion 21 of the base shell 13.

Figure 2:
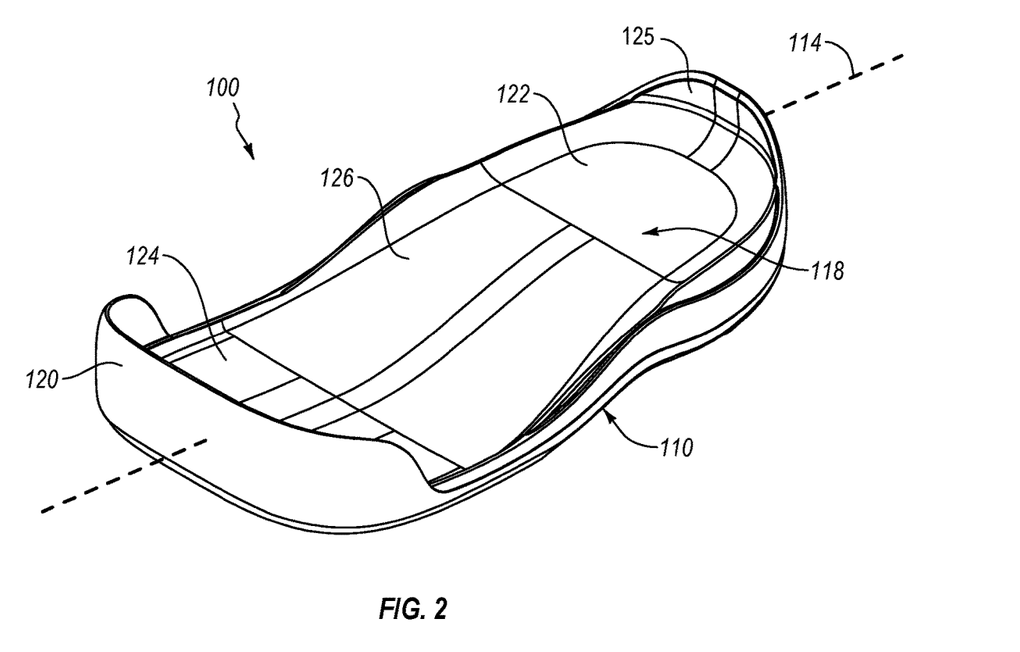
FIG. 2 is a top isometric view of an outsole according to an embodiment.
Figure 3:
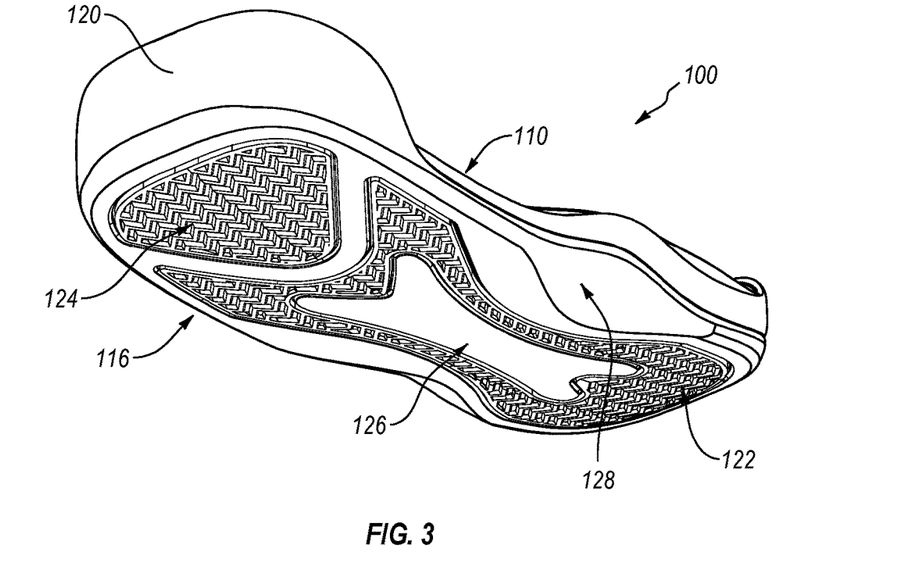
FIG. 3 is a bottom isometric view of the outsole shown in FIG. 2.
Figure 4:
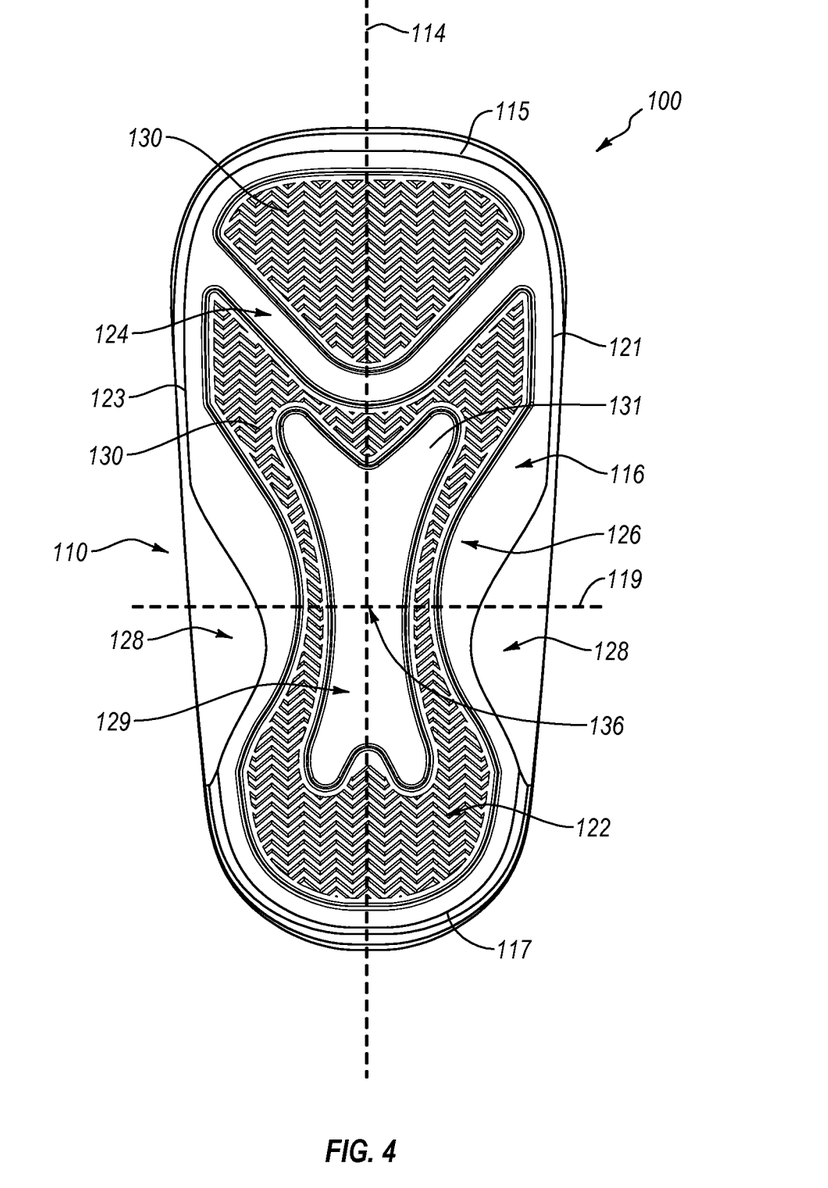
FIG. 4 is a bottom view of the outsole shown in FIG. 2.

The sole portion 110 is arranged to support the foot and contact a support surface during ambulation. As seen in FIGS. 2-4, the sole portion 110 can include a heel part 122, a forefoot part 124, and a mid-foot part 126 between the heel part 122 and the forefoot part 124. The thickness of the sole portion 110 in the heel part 122 can be greater than the thickness of the sole portion 110 in the forefoot part 124 (best shown in FIG. 7), improving the comfort and dimensional stability of the outsole 100 under the heel bone.

The sole portion 110 extends along a longitudinal axis 114 between an anterior end 115, which can correspond to the forefoot part 124, and a posterior end 117, which can correspond to the heel part 122. A transverse axis 119 extends across the width of the sole portion 110 between first and second edges 121, 123 of the sole portion 110 so that the transverse axis 119 intersects the longitudinal axis 114. The transverse axis 119 can extend generally transverse to the longitudinal axis 114 between the first edge 121 and the second edge 123. If the outsole 100 is being worn on the right foot, the first edge 121 can be a medial edge and the second edge 123 can be a lateral edge. If the outsole 100 is being worn on the left foot, the first edge 121 can be a lateral edge and the second edge 123 can be a medial edge.

The longitudinal axis 114 is shown generally corresponding to a midline of the sole portion 110 but can be located anywhere between the first and second edges 121, 123. The transverse axis 119 is shown extending through the mid-foot part 126 but can be located anywhere between the anterior end 115 and the posterior end 117.

Optionally, the bottom surface 116 of the sole portion 110 can include a pair of curved lengthwise contours that define raised arch portions 128 (best shown in FIG. 4) on opposite sides of the mid-foot part 126. By providing an arch portion 128 on both sides of the mid-foot part 126, the width of the outsole 100 at a user's mid-gait can be reduced to help prevent or limit the foot from being forced laterally or medially, which can create strain on the knee. One or more of the arch portions 128 may be less prominent or omitted.

The outsole 100 may be formed with any suitable material. For example, the outsole 100 may include a foam material such as EVA foam material. The EVA foam material can provide the outsole 100 with a light-weight and durable construction while concurrently providing the walker 11 with cushioning. Due to the relatively light-weight of the EVA foam material, the outsole 100 can include a relatively large thickness to provide increased protection to the foot of the wearer. Depending on the particular requirements for the walker 11, however, the outsole 100 may be formed for a variety of different materials, such as thermoplastic polyurethane (TPU), rubber, EVA cork, combinations thereof, or any other suitable material.

The bottom surface 116 of the sole portion 110 can include tread or other friction enhancing characteristics. The bottom surface 116 can define a tread section or pattern 130 that provides a grip between the bottom surface 116 and the support surface that contacts the outsole 100 during ambulation. The tread pattern 130 may be formed from one or more resilient polymeric materials (e.g., rubber, synthetic rubber, combinations thereof) or any other suitable materials that are set in the sole portion 110 of the outsole 100. This has the effect of providing the outsole 100 with traction and durability to extend the useful life of the outsole 100 and/or to make the outsole 100 safer.

The tread pattern 130 may be integrally formed in the sole portion 110 of the outsole 100. The tread pattern 130 can extend over discrete regions of the bottom surface 116. The tread pattern 130 can include a wedge-like portion in the forefoot part 124 and a generally foot-like shaped portion extending through the forefoot part 124, the mid-foot part 126, and the heel part 122. The foot-like shaped portion can include a cutout on an anterior edge thereof that is shaped to generally mate with the wedge-like portion in the forefoot part 124. The pattern of the tread section or pattern 130 can exhibit any arrangement. For example, the tread pattern 130 can include zig-zag like grooves in the forefoot part 124 and the heel part 122 and a plurality of slanted grooves and/or angled grooves in the mid-foot part 126. The tread pattern 130 can include zig-zag like grooves in the mid-foot part 126.

Optionally, the tread pattern 130 can include a recessed groove or slot extending along the peripheral portions of the tread pattern 130. The tread pattern 130 may be raised relative to other portions of the bottom surface 116 such that tread pattern 130 forms one or more high points on the bottom surface 116 thereby providing a primary wear surface area between the outsole 100 and the support surface or floor during ambulation.

The tread section 130 can define an interior region 129 that does not include a tread pattern and/or polymeric material. The region 129 is shown having an X-like configuration but can have any suitable configuration. The region 129 is arranged to help accommodate different lines of progression on the bottom surface 116 that are described below. This can help prevent wearing of the bottom surface 116 preferentially along the lines of progression by transferring and/or distributing at least some of the contact forces along the lines of progression to the surrounding tread pattern 130. Alternatively, the tread pattern 130 may be omitted or may cover the entire surface of the bottom surface 116 of the outsole 100.

The outsole 100 can be oversized relative to a conventional outsole. A width of the outsole 100 can be defined between the lateral and medial edges 123, 121 of the outsole 100. The width of the outsole 100 can be between about 1.02 and about 1.5, between about 1.05 and about 1.3 (e.g., about 1.08), or between about 1.1 and about 1.2 times greater than the width of a conventional outsole. This additional width can provide more stability than a conventional outsole. Widening the outsole 100 can also provide a greater overall range of apical lines described below along the bottom surface 116, which, in turn, can provide a greater overall range of lines of progression along which the user's foot can roll-over.

Figure 5:
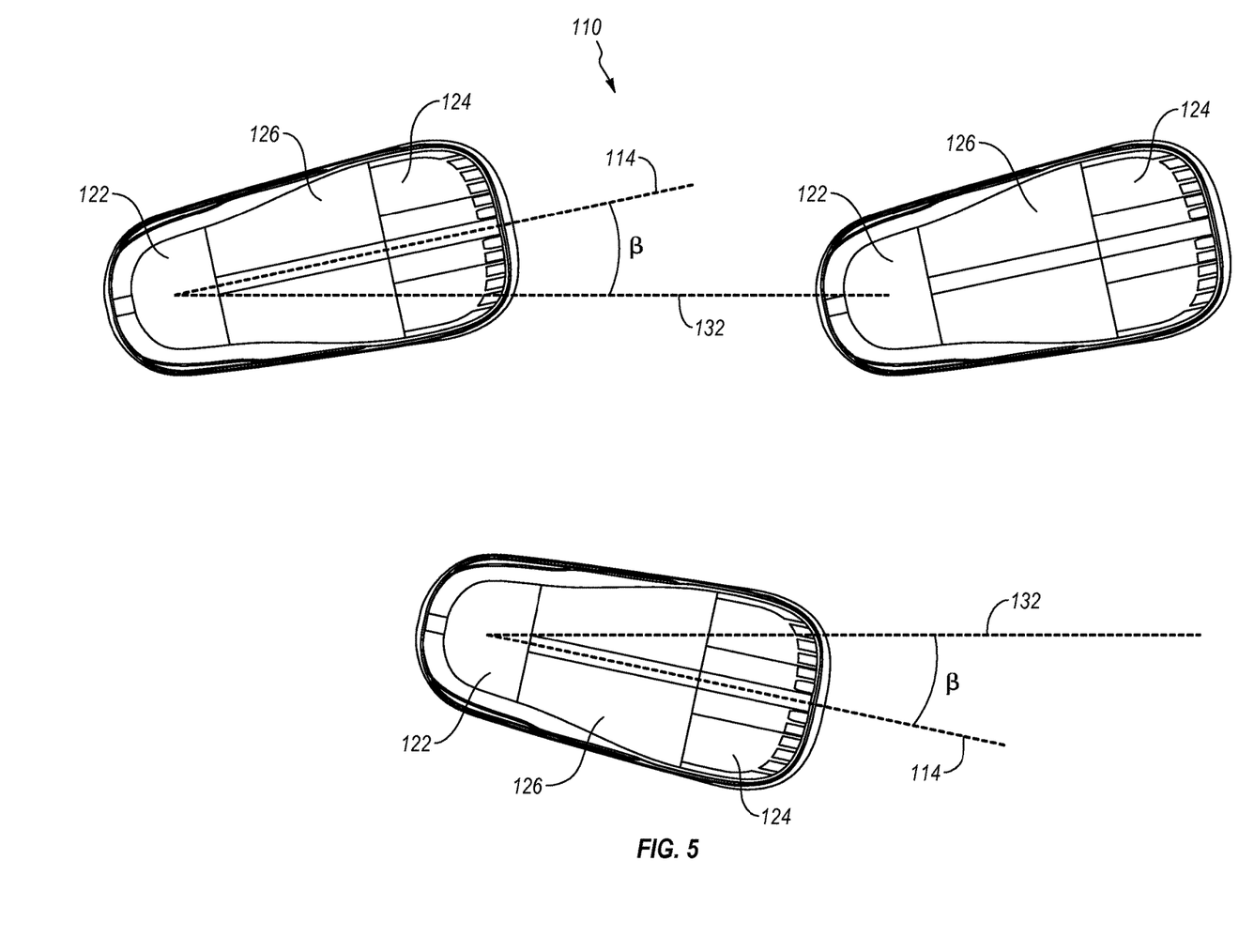
FIG. 5 is a schematic view of the outsole in ambulation according to an embodiment.

The bottom surface 116 of the outsole 100 may include one or more roll-over features arranged to make the act of ambulating smoother and easier for the user. Referring briefly to FIG. 5, a description of a few more terms is necessary. A line of progression is the line 132 connecting the same point on the bottom surface 116 of two consecutive footfalls of the same foot as the user ambulates wearing the outsole 100. "Toe in" or "toe out" is the angle β between the line of progression 132 and the midline (or the longitudinal axis 114 in this example) of the outsole 100. Angle β is zero if the midline of the outsole 100 is parallel to the line of progression 132. Angle β is positive or toe-out when the midline of the outsole 100 is on the lateral side of the line of progression 132. Angle β is negative or toe-in when the midline of the outsole 100 is on the medial side of the line of progression 132.

Known outsoles for walkers and other orthopedic devices are designed to force the line of progression of the foot directly from back to front along the longitudinal axis (e.g., with an angle β of zero). However, most people do not walk with their feet pointed straight ahead. Rather, most people walk with their feet toe-out. More specifically, most people walk with their feet between about 5 degrees and about 7 degrees toe-out or exorotated. By forcing the line of progression directly from back to front, known outsoles add stress and discomfort to the user as the user ambulates. Such stresses may adversely affect recuperation and/or cause undesirable biomechanical compensations which in the long term can cause problems. The linear roll-over motion of known outsoles also can cause foot and leg fatigue because the action of the outsoles conflict with the natural roll-over motion of the user, requiring the user to adjust or correct the position of the user's foot and/or causing muscle imbalances in the foot and/or leg.

The shape of the bottom surface 116 of the outsole 100 advantageously forms a roll-over surface that allows a user's foot to roll-over along exorotated or other lines of progression rotated relative to the longitudinal axis 114 with little or no resistance from the outsole 100. Because the bottom surface 116 accommodates the natural roll-over motion and gait of the user rather than forcing the foot straight ahead in a linear fashion as in the prior art, it provides a smoother and more comfortable ride for the user, decreasing the likelihood of injury and the likelihood of the user avoiding use of the outsole. It also decreases the likelihood of foot and/or leg fatigue because the outsole 100 moves with the user's foot during gait rather than conflicting with it.

Figure 6:
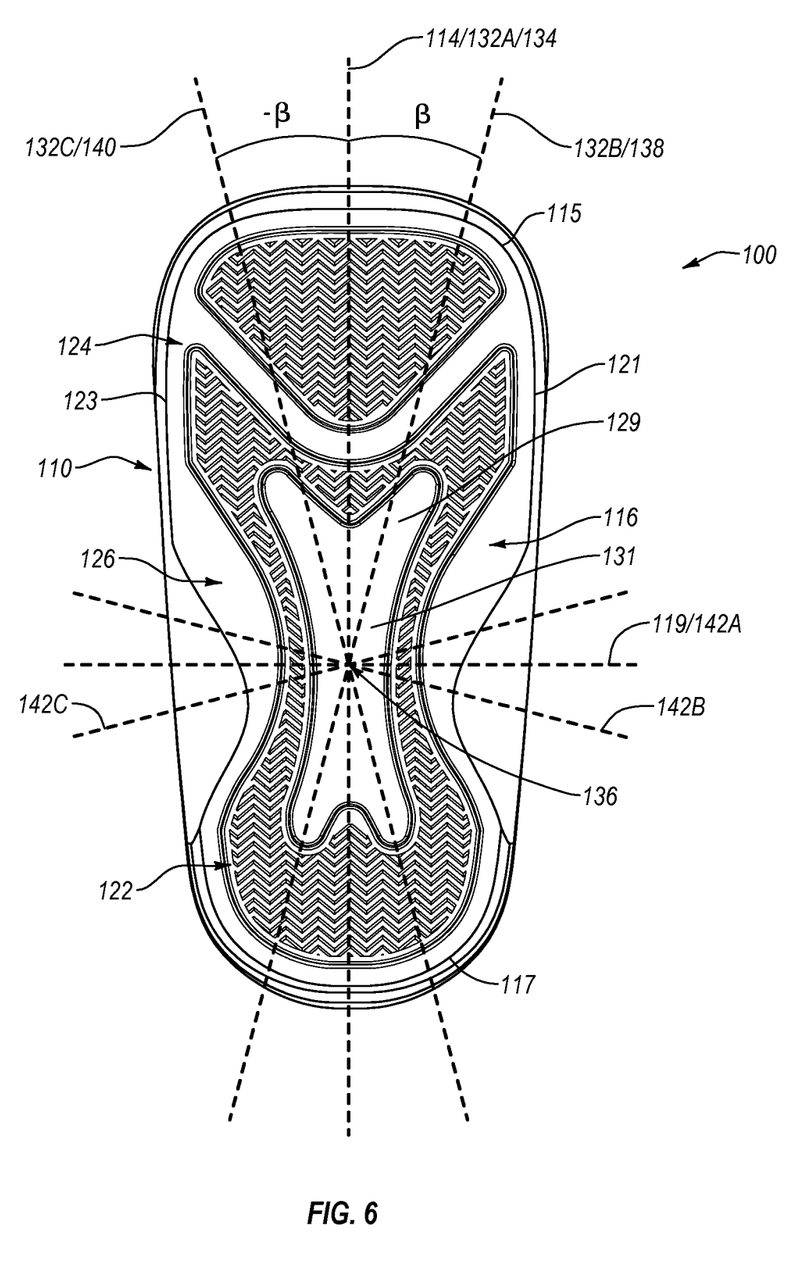
FIG. 6 is another bottom view of the outsole shown in FIG. 2 according to an embodiment.

As seen in FIG. 6, the bottom surface 116 of the outsole 100 includes an apex 136. The apex 136 is substantially or generally the lowest or most distal point of the bottom surface 116. The apex 136 can be located in any suitable location. The apex 136 can be located at the intersection of the longitudinal axis 114 and the transverse axis. The apex 136 can be located within the region 129. The apex 136 can be located in the mid-foot part 126 toward the heel part 122. The apex 136 can be located in the center of the mid-foot part 126. The apex 136 can be located in the forefoot part 124, the heel part 122, or in any other suitable location on the bottom surface 116. The bottom surface 116 may include one apex or a plurality of apexes.

Figure 7:
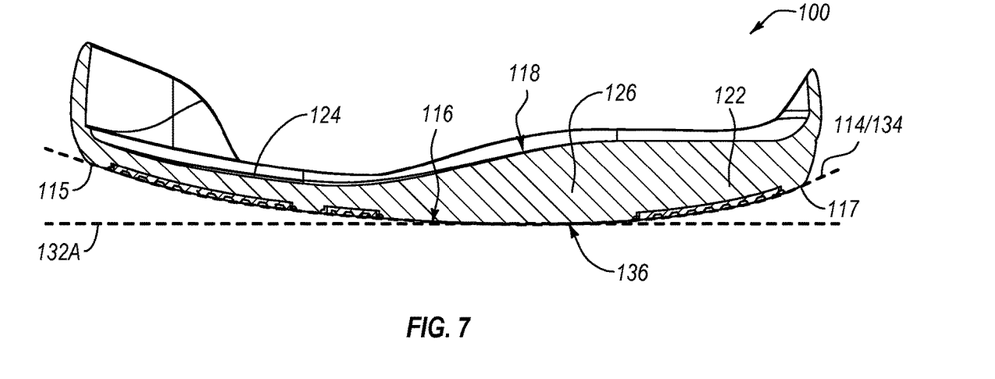
FIG. 7 is a cross-sectional view of the outsole shown in FIG. 2. taken along a first apical line according to an embodiment.

The bottom surface 116 can be curved in a longitudinal direction (e.g., about the transverse axis 119 or generally between the anterior end 115 and the posterior end 117) (see FIG. 7). For instance, the bottom surface 116 can curve in the longitudinal direction along the longitudinal axis 114 downward (e.g. away from the upper surface 118) from the heel part 122 through the apex 136 in the mid-foot part 126, and then upward (e.g., toward the upper surface 118) to the forefoot part 124. The radius of curvature of the bottom surface 116 along the longitudinal axis 114 can vary along the length longitudinal axis 114, increasing from the apex toward the anterior and posterior ends 115, 117. Thus the bottom surface 116 along the longitudinal axis 114 can be convexly curved.

The bottom surface 116 also can be curved in a transverse direction (e.g., about the longitudinal axis 114 or generally between the medial and lateral sides 121, 124). For instance, the bottom surface 116 can curve along the transverse axis 119 in the transverse direction across the width of the bottom surface 116, downward from the lateral edge 123 through the apex 136 and then upward toward the medial side 121. The radius of curvature of the bottom surface 116 along the transverse axis 119 can vary across the width of the bottom surface 116, increasing from the apex 136 toward the medial and lateral edges 121, 123. The bottom surface 116 along the transverse axis 119 can thus be convexly curved.

Because the bottom surface 116 curves in both the longitudinal direction and/or the transverse direction, the bottom surface 116 creates a roll-over surface that curves in different spatial directions rather than being curved linearly or solely from heel to toe as in the prior art. The bottom surface 116 can define any suitable curved surface in different spatial directions. The bottom surface 116 can form at least a portion of a generally ovoid surface, a generally ellipsoid surface, or any other suitable curved surface. For instance, the region 129 defines at least a portion of a substantially prolate spheroid (e.g., football) face 131. The face 131 extends through the apex 136 and is curved transversely and longitudinally. The bottom surface 116 can define a generally downwardly-facing convex face, providing a smoother and more comfortable ride for the user.

The curvature of the bottom surface 116 in the forefoot part 124 can exhibit a relatively smooth and/or constant radius extending to the anterior end 115 of the bottom surface 116. This can help provide a more comfortable fit by reducing pressure on the user's tibia from a dorsal shell of a walker. This is in contrast to conventional outsoles for orthopedic walkers which include a flat spot in the toe region that tends to urge the dorsal shell against the tibia as the dorsal shell becomes pitched or angled relative to the outsole at toe-off.

The bottom surface 116 can curve in the longitudinal and/or transverse directions along a plurality of apical lines extending through the apex 136, some of which can subtend oblique angles to the longitudinal axis 114 when view from below. For instance, the apical lines can include a first apical line 134 corresponding to the longitudinal axis 114. The bottom surface 116 can curve along the first apical line 134 downwardly from a center of the heel part 122, through the apex 136, and then upwardly through a center of the forefoot part 124, curving in the longitudinal direction.

The apical lines can include a second apical line 138 extending through apex 136 that subtends an oblique angle to the longitudinal axis 114. If the walker 11 is being worn on the right foot, the second apical line 138 extends from a lateral region of the heel part 122, through the apex 136, to a medial region of the forefoot part 124. The bottom surface 116 curves along the second apical line 138 downwardly from a lateral region of the heel part 122, through the apex 136, and then upwardly through a medial region of the forefoot part 124, curving in both the longitudinal and medial directions.

The apical lines can include a third apical line 140 extending through the apex 136 that subtends another oblique angle to the longitudinal axis 114. If the walker 11 is being worn on the right foot, the third apical line 140 extends from a medial region of the heel part 122, through the apex 136, to a lateral region of the forefoot part 124. The bottom surface 116 curves along the third apical line 140 downwardly from a medial region of the heel part 122, through the apex 136, and then upwardly through a lateral region of the forefoot part 124, curving in both the longitudinal and medial directions.

As described below, the different apical lines on the bottom surface 116 correspond or substantially correspond to a range of lines of progression along which the user's foot can possibly roll-over. This advantageously allows the user's foot to roll-over along exorotated or other lines of progression without being forced by the shape of the outsole to roll-over straight ahead from back to front as in the prior art, which, in turn, encourages a more natural and comfortable gait. This arrangement also conserves some of the energy of locomotion and returns energy to the user by smoothing out the gait cycle.

The apex 136 can serve as a fulcrum point or center of rotation of the outsole 100 when a user is ambulating. The fulcrum or center of rotation of the outsole 100 can be located away from the apex 136. For instance, the fulcrum or center of rotation of the outsole 100 can be located posterior the apex 136, anterior of the apex 136, medial and/or lateral of the apex 136, combinations thereof, or in any other suitable location on the bottom surface 116.

As a user wearing the walker 11 stands still, the sole portion 110 of the outsole 100 can rest on the ground on the mid-foot part 126 and the heel part 122. As the user takes a step, the apex 136 can act as a fulcrum or center of rotation so that the outsole 100 rolls forward off of the heel part 122 and onto the mid-foot part 126 and then the forefoot part 124.

The bottom surface 116 can define one or more roll-over axes associated with the different apical lines around which the outsole 100 rocks or rolls. As seen, the outsole 100 can include a first roll-over axis 142A extending through the apex 136 that is substantially perpendicular to the first apical line 134 or the longitudinal axis 114. During gait, rotation of the outsole 100 about the first roll-over axis 142A can permit the foot to roll over along a line of progression 132A corresponding to the first apical line 134. Because the bottom surface 116 is curved along first apical line 134 in the longitudinal direction, the user's foot can roll-over about the first roll-over axis 142A, straight ahead along the line of progression 132A and through the apex 136 with reduced or little resistance from the outsole 100.

A second roll-over axis 142B can be substantially perpendicular to the second apical line 138. During gait, rotation of the outsole 100 about the second roll-over axis 142B can allow the foot to roll over along a line of progression 132B corresponding to the second apical line 138. Because the bottom surface 116 curves along the second apical line 138 in both the longitudinal and transverse directions, the user's foot can roll-over along the line of progression 132B, which is rotated relative to the longitudinal axis 114, and through the apex 136 with reduced or little resistance from the outsole 100. The orientation of the second roll-over axis 142B can be generally indicative of the direction of curvature of the bottom surface 116 about the longitudinal axis 114 and the transverse axis 119 along the second apical line 138.

This advantageously facilitates a more natural roll-over motion of the user's foot from heel strike through toe-off. For instance, the line of progression 132B can be an exorotated line of progression. The line of progression 132B can be at an angle β relative to the longitudinal axis 114 or a sagittal plane of the outsole 100. The angle β can be between about 1 degree and about 10 degrees, between about 3 degrees and about 8 degrees, or between about 5 degrees and about 7 degrees. It will be appreciated that the angle β can be larger or smaller and that if the walker 11 is being worn on the left foot, the line of progression 132B can allow the outsole to roll-over with the user's foot from heel strike to toe-in. It will also be appreciated that the angle β can be selected based on the specific gait of a user. The angle β can be selected based on a typical gait of a user. The angle β can be selected based on a desired treatment protocol.

As seen, the outer periphery of the region 129 can taper inward from a posterior end of the region 129 toward the apex 136 and can expand from the apex 136 toward an anterior end of the region 129. This can help direct the roll-over motion of the foot toward the apex 136 and can help limit inference from the tread section 130 beyond the apex 136 when the roll-over motion is along a line of progression that is rotated relative to the longitudinal axis 114. For instance, during heel strike, the user's weight can move towards the posterior lateral edge of the region 129. As the user's weight moves forward, the user's weight is directed through the region 129 inwardly toward the apex 136 and downwardly along the line of progression 132B. In the mid stance phase, the user's weight moves along the line of progression 132B through the apex 136. In the toe-off phase, the user's weight moves outwardly from the apex 136 toward the anterior medial edge of the region 129 and upwardly along the line of progression 132B.

As the user's weight moves through the region 129, the face of the region 129 provides a smoother surface than the tread section 130 surrounding the region 129 for the user's foot to roll-over on, smoothing out the user's ride. Further, the tread section 130 surrounding the region 129 can transfer and/or distribute at least some of the user's weight along the line of progression 132B away from the region 129 and to the surrounding tread section 130. This can help prevent wearing of the bottom surface 116 preferentially along the line of progression 132B. It will be appreciated that the same or similar principles can be applied along the line of progression 132C and/or other lines of progression extending through the region 129.

A third roll-over axis 142C can be substantially perpendicular to the third apical line 140. During gait, rotation of the outsole 100 about the third roll-over axis 142C can allow the foot to roll over along a line of progression 132C corresponding to the third apical line 140. Because the bottom surface 116 is curved along the third apical line 140 in both the longitudinal and transverse directions, the user's foot can roll-over along the line of progression 132B, which is rotated relative to the longitudinal axis 114 and through the apex 136 with reduced or little resistance from the outsole 100. The orientation of the third roll-over axis 142C can be generally indicative of the direction of curvature of the bottom surface 116 about the longitudinal axis 114 and the transverse axis 119 along the third apical line 140.

The line of progression 132C can be at an angle −β relative to the longitudinal axis 114. The angle −β can be between about −1 degree and about −10 degrees, between about −3 degrees and about 8 degrees, or between about −5 degrees and about 7 degrees. It will be appreciated that the angle −β can be larger or smaller. Again, it will be appreciated that if the walker 11 is being worn on the left foot, the user's foot can roll over from heel strike to toe-out at toe-off along the line of progression 132C. While the roll-over axes 142A, 142B, 142C are shown and described extending through the apex 136, the roll-over axes can be positioned and oriented to extend through the longitudinal axis 114 posterior of the apex 136, through the longitudinal axis 114 anterior of the apex 136, or through any other suitable location on the outsole 100.

The longitudinal and transverse curvature of the bottom surface 116 along the different apical lines permit the foot to roll-over along different lines of progression. This beneficially helps prevent or limit the foot from being forced straight ahead from forward to back by the outsole, reducing the likelihood of strain on the knee and making the act of ambulating more natural and easier for the user. It may also be beneficial to reduce loads on the ankles, toes and metatarsals.

In the illustrated embodiment, the radius of curvature of the bottom surface 116 can be the same or approximately the same along different apical lines extending through the apex 136. For instance, FIG. 7 is a cross-sectional view of the outsole 100 taken along the first apical line 134. Along the first apical line 134, the bottom surface 116 curves downwardly relative to the upper surface 118 in the heel part 122. The bottom surface 116 then curves through the apex 136 in the mid-foot part 126 and upwardly through the forefoot part 124. The radius of curvature of the bottom surface 116 varies along the first apical line 134, decreasing from the posterior end 117 to the apex 136 and increasing from the apex 136 to the anterior end 115.

Figure 8:
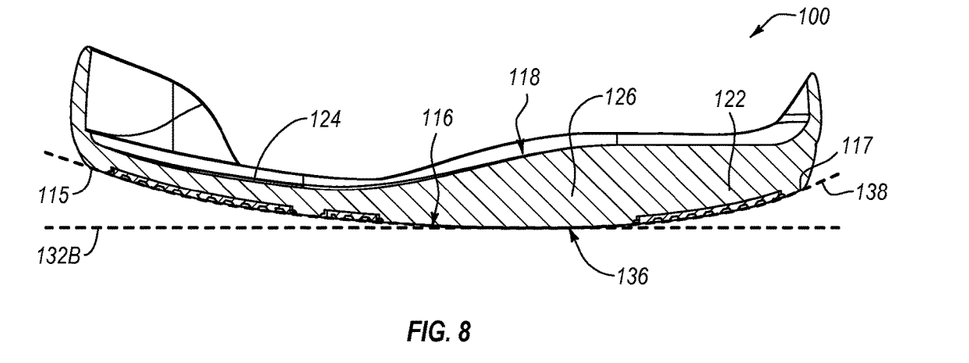
FIG. 8 is a cross-sectional view of the outsole shown in FIG. 2. taken along a second apical line according to an embodiment.

FIG. 8 is a cross-sectional view of the outsole 100 taken along the second apical line 138. Along the second apical line 138, the bottom surface 116 curves downwardly relative to the upper surface 118 in the heel part 122. The bottom surface 116 then curves through the apex 136 in the mid-foot part 126 and upwardly through the forefoot part 124. As seen in FIGS. 7 and 8, the radius of curvature of the bottom surface 116 along the first apical line 134 can be similar to or approximately the same as the radius of curvature of the bottom surface 116 along the second apical line 138.

Figure 9:
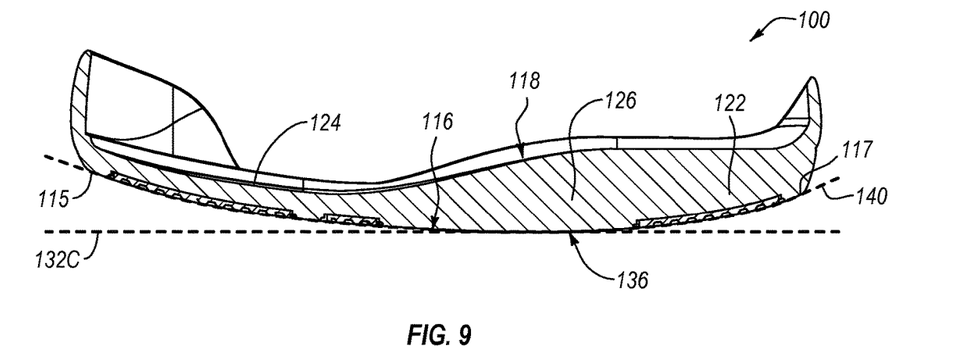
FIG. 9 is a cross-sectional view of the outsole shown in FIG. 3 taken along a third apical line according to an embodiment.

FIG. 9 is a cross-sectional view of the outsole 100 taken along the third apical line 140. Along the third apical line 140, the bottom surface 116 curves downwardly relative to the upper surface 118 in the heel part 122. The bottom surface 116 then curves through the apex 136 in the mid-foot part 126 and upwardly through the forefoot part 124. As seen in FIGS. 8 and 9, the radius of curvature of the bottom surface 116 along the second apical line 138 can be similar to or approximately the same as the radius of curvature of the bottom surface 116 along the third apical line 140.

Because the radius of curvature of the bottom surface 116 along the different apical lines is the same or substantially the same, the user's foot can experience the same or a similar roll-over motion on the outsole 100 along the different lines of progression corresponding to the apical lines. For instance, the user's foot can roll over along the line of progression 132A corresponding to the first apical line 134 or the line of progression 132B corresponding to the second apical line 138 and experience the same or very similar roll-over motion. Alternatively, the user's foot can roll over along the line of progression 132A corresponding to the first apical line 134 or the line of progression 132C corresponding to the third apical line 140 and experience the same or very similar roll-over motion. This has the beneficial effect of encouraging a more natural roll over of the foot because the foot can just as easily and comfortably roll over along one line of progression as another.

In other embodiments, the radius of curvature of the bottom surface can be varied to vary the roll-over motion of user's foot on the outsole 100. For instance, the radius of curvature along a first apical line or a second apical line can be greater than the radius of curvature along another apical line to exorotate or urge the user to walk toe-out, or toe-in. It will be appreciated that the curvature can vary along the apical lines. For example, a first apical line can have a first portion having a first radius of curvature and a second portion having a second radius of curvature that is different from the first radius of curvature.

Figure 10:
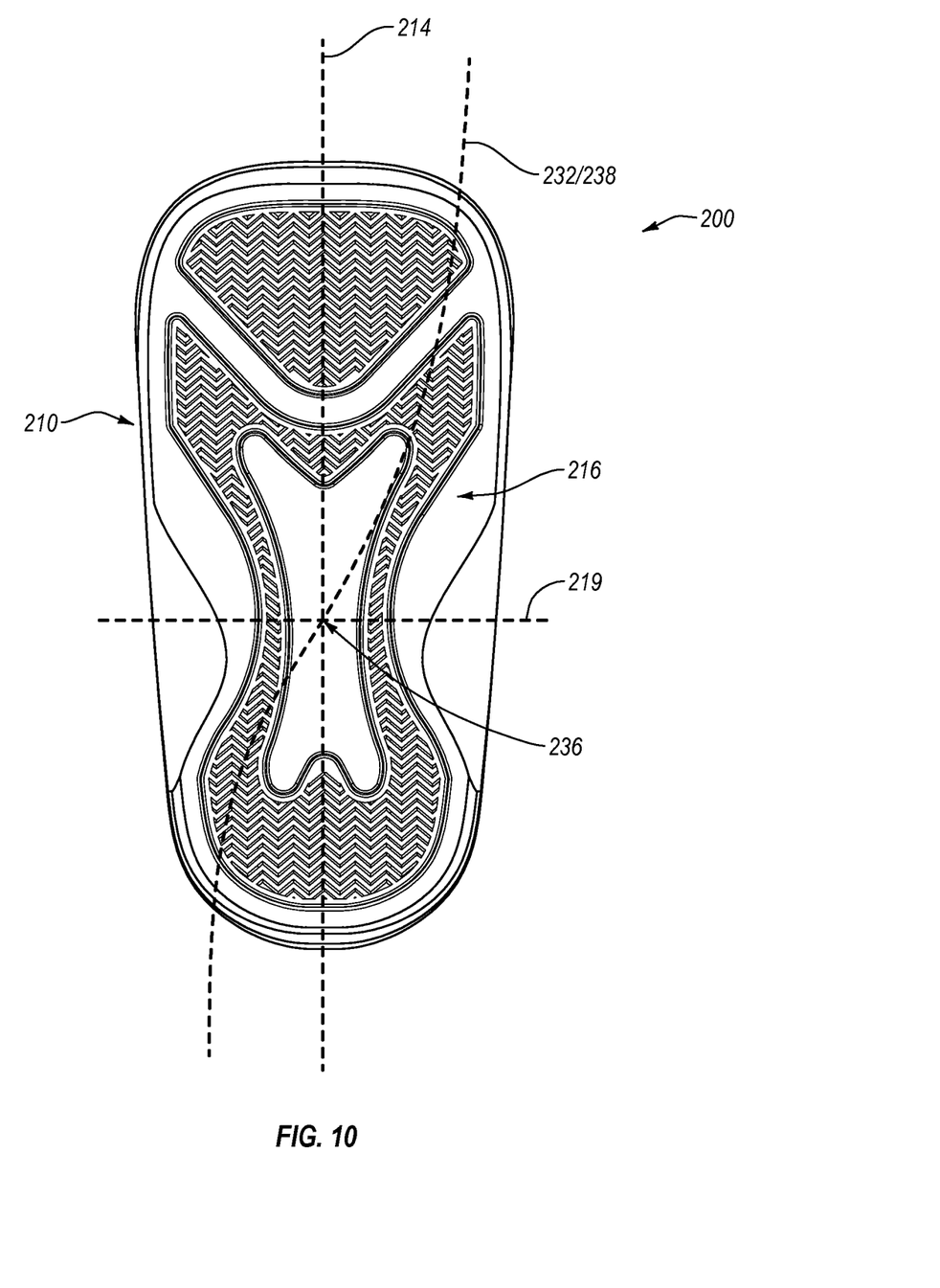
FIG. 10 is a bottom view of an outsole according to another embodiment.

While the lines of progression are shown being substantially linear, in other embodiments, the bottom surface of the outsole can be curved to accommodate one or more non-linear lines of progression. For instance, FIG. 10 illustrates an outsole 200 including a sole portion 210 having a bottom surface 216 defining a longitudinal axis 214, a transverse axis 219 intersecting the longitudinal axis 214, and an apex 236. The bottom surface 216 can include an apical line 238 curving and turning through the apex 236. The apical line 238 corresponds to at least one line of progression 232, both having one or more non-linear portions rotated relative to the longitudinal axis 214.

The configuration of the outsole described herein is to be regarded as exemplary only, as any suitable configuration of the outsole is possible. For example, while three apical lines are shown and described, in other embodiments, the outsole can include two, four, five, or any other suitable numbers of apical lines. Further, in other embodiments, different apical lines can have varying curvatures. Moreover, in other embodiments, the apical lines can extend through more than one apex on the bottom surface.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An outsole for an orthopedic device comprising:
a heel part, a forefoot part, and a mid-foot part separating the heel part from the forefoot part;
a longitudinal axis extending in a longitudinal direction between an anterior end of the forefoot part and a posterior end of the heel part;
a transverse axis intersecting the longitudinal axis and extending in a transverse direction between a lateral edge of the outsole and a medial edge of the outsole;
an upper surface, a bottom surface, and a thickness defined between the upper and bottom surfaces, the bottom surface extending along the longitudinal axis and between the medial and lateral edges, the bottom surface defining an apex at the intersection of the longitudinal axis and the transverse axis and at least one apical line passing through the apex and subtending an oblique angle to the longitudinal axis, wherein the apex is located at a maximum thickness of the outsole and the bottom surface curves through the apex and along the at least one apical line in both the longitudinal direction and the transverse direction and the bottom surface defines a substantially same radius of curvature along the at least one apical line and the longitudinal axis; and
a tread section on the bottom surface including a tread pattern comprising a plurality of angled grooves surrounding an interior region including the apex; the interior region being smoother than the tread pattern, the tread section arranged so that when weight is placed on the outsole over the interior region the tread section distributes at least some of the weight away from the interior region to the tread section
the interior region surrounding the apex and having an outer periphery defining a saltire shape tapering inward from a posterior end of the interior region to the apex and expanding outward from the apex toward an anterior end of the interior region so that the interior region directs a heel strike of a foot of a user toward the apex and limits interference by the tread pattern from a mid-stance of the foot toward a toe-off of the foot.

2. The outsole of claim 1, wherein the oblique angle is between about 5 degrees and about 7 degrees.

3. The outsole of claim 1, wherein the bottom surface curves in the transverse and longitudinal directions from the apex in the direction of the lateral edge.

4. The outsole of claim 1, wherein the bottom surface curves downwardly along the at least one apical line from the direction of the lateral edge of the heel part toward the apex.

5. The outsole of claim 1, wherein the bottom surface curves upwardly along the at least one apical line from the apex toward the medial edge of the forefoot part.

6. The outsole of claim 1, wherein the at least one apical line includes a first apical line and a second apical line intersecting the first apical line at the apex, the second apical line subtending another oblique angle to the longitudinal axis.

7. The outsole of claim 6, wherein a radius of curvature of the bottom surface along the first apical line is substantially the same as a radius of curvature of the bottom surface along the second apical line.

8. The outsole of claim 1, wherein the interior region defines a prolate spheroid face on the bottom surface.

9. The outsole of claim 1, wherein the at least one apical line extends diagonally through the interior region.

10. The outsole of claim 1, wherein the apex is located in the mid-foot part.

11. The outsole of claim 1, wherein the upper surface is arranged for attachment to a plantar portion of an orthopedic device; and further comprising a toe protector portion extending generally upright from the upper surface at the anterior end of the forefoot part.

12. The outsole of claim 11, wherein the thickness of the outsole between the upper surface and the bottom surface in the heel part is greater than the thickness of the outsole between the upper surface and the bottom surface in the forefoot part.

13. An outsole for an orthopedic device comprising:
a heel part,
a forefoot part;

a mid-foot part separating the heel part from the forefoot part;
a longitudinal axis extending between an anterior end of the forefoot part and a posterior end of the heel part;
a transverse axis intersecting the longitudinal axis and extending between a lateral edge of the outsole and a medial edge of the outsole;
an upper surface, a bottom surface, and a thickness defined between the upper and bottom surfaces, the bottom surface defining an apex on the mid-foot part and at least one apical line passing through the apex and subtending an oblique angle to the longitudinal axis, wherein the apex is located at a maximum thickness of the outsole and the bottom surface curves through the apex about both the longitudinal axis and the transverse axis and the bottom surface defines a substantially same radius of curvature along the least one apical line and the longitudinal axis; and
a tread section on the bottom surface including a tread pattern comprising a plurality of angled grooves surrounding an interior region including the apex; the interior region being smoother than the tread pattern, the tread section arranged so that when weight is placed on the upper surface of the outsole over the interior region the tread section distributes at least some of the weight away from the interior region to the tread section
the interior region surrounding the apex and having an outer periphery defining a saltire shape tapering inward from a posterior end of the interior region to the apex and expanding outward from the apex toward an anterior end of the interior region so that the interior region directs a heel strike of a foot of a user toward the apex and limits interference by the tread pattern from a mid-stance of the foot toward a toe-off of the foot.

14. The outsole of claim 13, wherein the bottom surface curves upward toward the upper surface from the apex and in the direction of the medial edge of the forefoot part.

15. The outsole of claim 14, wherein the bottom surface curves upward toward the upper surface from the apex and in the direction of the anterior end of the forefoot part.

16. An orthopedic device comprising:
a base shell having a plantar portion and forming an opening in an anterior aspect thereof,
a dorsal shell contoured to generally correspond to the opening of the base shell; and
an outsole including:
an upper surface secured to the plantar portion of the base shell; and
a bottom surface opposite the upper surface, the bottom surface extending along a longitudinal axis between an anterior end of the outsole and a posterior end of the outsole;
a thickness defined between the upper and bottom surfaces;
a transverse axis intersecting the longitudinal axis and extending in a transverse direction between a lateral edge of the outsole and a medial edge of the outsole;
an apex on the bottom surface at the intersection of the longitudinal axis and the transverse axis, the apex located at a maximum thickness of the outsole;
at least one apical line passing through the apex and subtending an oblique angle to the longitudinal axis, wherein the bottom surface curves about both the longitudinal axis and the transverse axis through the apex and defines a substantially same radius of curvature along the at least one apical line and the longitudinal axis; and
a tread section on the bottom surface including a tread pattern comprising a plurality of angled grooves surrounding an interior region including the apex; the interior region being smoother than the tread pattern, the tread section arranged so that when weight is placed on the upper surface of the outsole over the interior region the tread section distributes at least some of the weight away from the interior region to the tread section
the interior region surrounding the apex and having an outer periphery defining a saltire shape tapering inward from a posterior end of the interior region to the apex and expanding outward from the apex toward an anterior end of the interior region so that the interior region directs a heel strike of a foot of a user toward the apex and limits interference by the tread pattern from a mid-stance of the foot toward a toe-off of the foot.

17. The orthopedic device of claim 16, wherein the radius of curvature of the bottom surface along the at least one apical line varies.

* * * * *